United States Patent [19]
Royle et al.

[11] Patent Number: 5,098,844
[45] Date of Patent: Mar. 24, 1992

[54] METHOD FOR ISOLATING PALYNOLOGICAL MATERIAL FROM A ROCK SAMPLE IN A PRESSURIZED REACTION CELL

[75] Inventors: Rae A. Royle; David G. Nolte, both of Houston, Tex.

[73] Assignee: Texaco Inc., White Plains, N.Y.

[21] Appl. No.: 461,511

[22] Filed: Jan. 5, 1990

[51] Int. Cl.$^5$ .................. G01N 33/24; G01N 24/00; G01N 1/18

[52] U.S. Cl. .................................... 436/31; 436/174; 436/177

[58] Field of Search ................ 436/177, 31, 174; 208/391, 430, 435, 404; 44/620, 621, 624

[56] References Cited

U.S. PATENT DOCUMENTS 4,093,420  6/1978  Grayson et al. .................. 436/31

OTHER PUBLICATIONS

Grayson, "Relationship of Palynomorph Translucency to Carbon and Hydrocarbons in Clastic Sediments", (1973), pp. 261-273.

*Primary Examiner*—David L. Lacey
*Assistant Examiner*—William Chan
*Attorney, Agent, or Firm*—Jack H. Park; Kenneth R. Priem; Harold J. Delhommer

[57] ABSTRACT

The invention is a method for the isolation of palynological materials from a rock sample in a pressurized reaction cell, which permits reaction at pressures greater than two atmospheres and provides for the removal of all liquids from the cell without significant loss of sample solids, the method employing multiple steps of addition and removal of concentrated and dilute hydrochloric acid, concentrated hydrofluoric acid, concentrated ammonium hydroxide, concentrated nitric acid and deionized water, followed by centrifugation and zinc bromide separation steps.

21 Claims, No Drawings

METHOD FOR ISOLATING PALYNOLOGICAL MATERIAL FROM A ROCK SAMPLE IN A PRESSURIZED REACTION CELL

BACKGROUND OF THE INVENTION

This invention is related to a method for isolating palynological material from rock samples. More particularly, the invention is concerned with a method useful for isolating pollen and spores in a pressurized reaction cell which provides for the removal of all liquids from the cell without significant loss of sample, followed by centrifugation and zinc bromide separation steps.

Palynological analysis has become an important part of petroleum exploration over the last two decades. Samples of palynological material are used to age-date the levels of rock in underground formations. Fossil spores and pollen have become important as keys for correlation and progressive evolution through time of rock sequences. Particular species of plants and microorganisms may serve as good indices of a certain interval of geoological time by virtue of having arisen by evolution early in the geological interval and having disappeared through extinction at the end of the geological interval.

The isolation of spores and pollen from the mineral matrix of rocks and outcrops is a very time consuming and labor intensive process. Current methods for palynological isolation take two to three weeks to perform as well as considerable attention by a laboratory technician.

A good number of the process steps involved in palynological isolation are the same or similar to the process steps involved in the isolation of kerogen from rock. Kerogen is a solid form of organic matter found in sedimentary rock that is insoluble in water, non-oxidizing acids and bases, and the usual organic solvents. It thermally degrades in a predictable manner by releasing hydrocarbons and condensing the solid organic structure. Because of its immobility, it can provide direct historical evidence of geological conditions within a stratigraphic sequence.

Kerogen, the precursor to oil and gas, must be isolated in such a way that the isolated fraction is as representative as possible of in situ kerogen. Analysis requires the recovery of a sufficient amount of kerogen sample without chemical alteration. A principle objective is to keep the morphology of the kerogen intact and to recover identifiable organic debris such as palynological material.

The isolation of kerogen and palynological material is a complicated chemical process that involves the use of strong acids and bases that dissolve the rock matrix without modifying the desired products. The rock sample is first finely ground to pea-sized particles approximately 1-2 mm in diameter in order to facilitate reaction with the reagents. The methods now used for kerogen isolation employ the dissolution of silicates by hydrofluoric acid and the dissolution of sulfides, sulphates, carbonates, oxides and hydroxides by hydrochloric acid. The reactions are normally carried out below 70° C., a temperature sufficient to dissolve carbonates, but inadequate to promote oxidation and degradation of the organic matter. For a general discussion of the methods of kerogen and palynological material isolation and reagents employed, please see Durand, B., Editor, Kerogen, Graham & Trotman Ltd, London (1980), especially Chapter 2, "Procedures for Kerogen Isolation" by Durand, B. and Nicaise, G., p. 35-52, and Chapter 3, "Les Kerogenes Vus Au Microscope" by Combaz, A., p. 58-60.

Generally the acid and base reactions are carried out in open plastic beakers placed in a steam bath to raise reaction temperature. After reaction, the aqueous liquids are removed from the beakers by decanting. The reaction steps are repeated until isolation is judged to be relatively complete. This usually takes anywhere from two to four weeks depending on the quality requirements of subsequent analyses and the type of rock being dissolved.

The process of decanting as well as the length of the procedure leaves much to be desired. A disadvantage to current isolation techniques is that a percentage of the kerogen and palynological material is frequently lost during decanting. Second, since aqueous liquids are never completely removed from the beakers, solvated metal and silicate ions are available as reactants to form fluoride precipitates. Once precipitated, these neoformed fluorides are virtually impossible to dissolve and remove without damaging the remaining kerogen. Third, beakers permit exposure to oxygen which creates undesirable oxidation products.

Other difficulties exist with current isolation procedures. Dangers to the workers who perform isolations in the standard open beaker method include exposure to hazardous highly concentrated hydrofluoric and hydrochloric acids and bases such as ammonium hydroxide, all of which must be added and decanted manually. Use of such chemicals requires not only protective personal equipment but also engineering controls such as hoods and other vacuum equipment.

SUMMARY OF THE INVENTION

The invention is a method for the isolation of palynological material from a mineral matrix sample in a pressurized reaction cell, which comprises multiple reaction steps between acid and base reagents and the mineral sample placed within a pressurized reaction cell, followed by centrifigation and zinc bromide separation steps. The reaction cell must permit reaction at pressures greater than about two atmospheres and provide for removal of all liquids from the cell without significant loss of sample solids. The ability to perform isolation reaction steps under pressure permits the use of elevated reaction temperatures.

The isolation method starts by adding a mixture of concentrated hydrochloric acid and deionized water to the reaction cell. After the desired period of reaction, the mixture is removed and concentrated hydrochloric acid is added to the reaction cell. After the desired reaction time, the hydrochloric acid is removed from the reaction cell and the reaction cell is flushed with deionized water to remove any remaining metal ions and to bring the sample relatively close to neutrality.

Concentrated ammonium hydroxide is added to the reaction cell for reaction and removed. Concentrated hydrofluoric acid is added to the reaction cell for reaction and removed. Concentrated hydrochloric acid is added to the reaction cell, reacted and removed, prior to flushing the reaction cell with deionized water. Concentrated ammonium hydroxide is added to the reaction cell for reaction and removed.

Concentrated hydrofluoric acid is added to the reaction cell, reacted and removed, and the cell flushed with deionized water. Concentrated ammonium hydroxide is added to the reaction cell, reacted and removed, and the cell flushed with deionized water. Concentrated hydrochloric acid is added to the reaction cell, reacted and removed, prior to flushing the reaction cell with deionized water. Concentrated ammonium hydroxide is added to the reaction cell, reacted and removed, and the cell flushed with deionized water. Concentrated nitric acid is added to the reaction cell, reacted and removed, and the cell flushed with deionized water.

The sample solids are then transferred to a centrifuge tube where they are centrifuged in dilute hydrochloric acid (about 4 to about 10 moles/liter) at about 2000 to about 3500 rpm for about 5 to about 20 minutes in a benchtop centrifuge. All liquid is removed from the centrifuged tube and a solution of zinc bromide in deionized water is added to the tube, said solution having a density of about 1.7 gm/ml. The solution and sample are mixed and centrifuged at about 500 to about 2000 rpm for about 10 to about 40 minutes.

The sample and solution are allowed to rest until layers formed within the tube are clearly separated. The top floating layer of organic light material comprising spores and pollen is transferred to a second centrifuge tube in dilute hydrochloric acid and centrifuged at about 2000 to about 3500 rpm for about 5 to about 20 minutes. The spores and pollen are washed at least one time with deionized water and centrifuged to remove the water phase. The desired palynological sample is then suspended in sufficient deionized water for microscopical examination.

DETAILED DESCRIPTION

The present technology for isolating palynological material involves complex manual processing of rock materials using the combination of acids, bases, reducing and oxidizing agents and organic solvents followed by multiple separation steps. The process is intended to isolate the desired pollen and spores without damaging the organic matter in the process. Current procedure is tied to the use of manual isolation process steps involving beakers open to the atmosphere and requiring decanting of all fluids after settling of the samples for each reagent addition step. The lengthy time of about two to four weeks required to isolate such palynological material with presently known processes is perhaps the most notable disadvantage. The instant invention process employed with a pressurized reaction cell permitting complete removal of liquids offers a process which can isolate palynological material in about 2 to 3 days.

The invention method requires first placing the mineral sample in a reaction cell, said reaction cell permitting reaction at pressures greater than about two atmospheres and providing for removal of all liquids from the cell without significant loss of sample solids. It is preferred that the reaction cell provide for the removal of reagents and dissolved materials by drainage through a filter at the bottom of the reaction cell.

It is also preferred that the invention process be run at elevated temperatures of about 45° C. to about 65° C. Such higher reaction temperatures substantially shorten the digestion times needed to remove undesired material from the rock sample. However, the reaction steps cannot be accomplished at these higher temperatures without maintaining the reaction cell under pressure of at least 2 atmospheres, preferably about 2.5 atmospheres to about 5 atmospheres. At higher temperatures and lower pressures, the concentrated acids and bases required will lose substantial strength through evaporation.

The first step involves adding a mixture of concentrated hydrochloric acid and deionized water to the reaction cell. Preferably the mixture is within the range of about ⅛ to 3/1 concentrated hydrochloric acid to deionized water, and is allowed to digest for a time greater than about 15 minutes, preferably about 30 minutes at 50° C. to about 60° C. and about 3 atmospheres of pressure. The concentrated hydrochloric acid is preferably about 10 to about 12 molar concentration.

For all reaction steps of the invention, it should be noted that required reaction times will vary greatly depending upon several factors including the concentration of the reagents, the temperature and pressure of the reaction, and the type and the amount of compounds within the mineral sample. For example, a higher reaction temperature may substantially decrease the needed reaction time. Furthermore, preferred reaction times are always longer than required reaction times since it is desirable to have a safe margin in the reaction time to insure removal of undesired compounds from the mineral sample. And when necessary, due to the presence of greater than usual amounts of certain compounds, reaction times may be extended or several groups of process steps may be repeated.

After the desired reaction time, the mixture of concentrated hydrochloric acid and deionized water is removed from the reaction cell to remove highly reactive aragonite, calcites, calcium and magnesium ions. Concentrated hydrochloric acid is then added to the reaction cell for a preferred reaction time greater than about 45 minutes, most preferably about 90 minutes at the desired temperature and pressure ranges of about 3 atmospheres and 50° C. to 60° C. As previously stated, the hydrochloric acid is preferably of a concentration of about 10 to about 12 moles per liter. The hydrochloric acid is removed from the reaction cell to remove slowly reacting carbonates and undesirable metal ions.

The reaction cell is flushed with deionized water to remove any remaining metal ions and to bring the sample relatively close to neutrality. Preferably, the flushing is done continuously for a time greater than about 15 minutes, most preferably for about 30 minutes.

Concentrated ammonium hydroxide is added to the reaction cell for a preferred reaction time greater than about 15 minutes, most preferably about 30 minutes at the most preferred temperature, (50°–60° C.) and pressure ranges (3 atmospheres) stated above. The concentrated ammonium hydroxide preferably has a concentration of about 10 to about 20 moles per liter. The ammonium hydroxide is removed from the reaction cell to remove silicate ions and base soluble organics and inorganics. The reaction cell is then flushed with deionized water as before.

Concentrated hydrofluoric acid is added to the reaction cell for a preferred reaction time greater than about 45 minutes in a preferred concentration of about 13 to about 35 moles per liter, most preferably about 90 minutes at about 13 to about 20 moles per liter. After reaction, the hydrofluoric acid is removed along with dissolved silicate and fluoride minerals and certain fluorinated compounds.

Concentrated hydrochloric acid is then added to the reaction cell and permitted to react for a preferred time greater than about 45 minutes, most preferably about 90 minutes. The hydrochloric acid is then removed from the reaction cell along with dissolved chlorinated and fluorosilicate compounds, and the reaction cell is flushed with deionized water.

Concentrated ammonium hydroxide is added to the reaction cell and permitted to react preferably for a time greater than about 15 minutes, most preferably about 30 minutes. The ammonium hydroxide has a preferred concentration of about 10 to about 20 moles per liter. Gel-formed silicas and silicates are removed from the reaction cell along with ammonium hydroxide.

Concentrated hydrofluoric acid is added to the reaction cell for a second time for a preferred reaction time greater than about 45 minutes in a concentration of about 13 to about 35 moles per liter, most preferably for about 90 minutes for about 13 to about 20 moles per liter. After reaction, the hydrofluoric acid is removed from the reaction cell, and the cell is flushed with deionized water to remove ions and bring the sample solids relatively close to neutrality.

Concentrated ammonium hydroxide is added to the reaction cell and reaction permitted preferably for a time greater than about 15 minutes, most preferably about 90 minutes. The ammonium hydroxide is removed from the reaction cell, and the cell is flushed with deionized water to remove ions and bring the sample solids relatively close to neutrality. Concentrated hydrochloric acid is then added to the reaction cell and permitted to react for a preferred time greater than about 45 minutes, most preferably about 90 minutes. The hydrochloric acid is removed from the reaction cell, and the cell is flushed with deionized water to remove ions and bring the sample solids relatively close to neutrality.

Concentrated ammonium hydroxide is again added to the reaction cell, and reaction is permitted for a preferred time greater than about 15 minutes, most preferably about 30 minutes. The ammonium hydroxide is removed from the cell and the cell is flushed with deionized water.

Concentrated nitric acid is then added to the reaction cell, and reaction is permitted for a preferrred time greater than about ten minutes at about 45° C. to about 65° C., most preferably about 20 minutes. The nitric acid is removed from the reaction cell and the cell is flushed with deionized water to remove ions and bring the sample solids relatively close to neutrality. This step ends the use of the reaction cell in the palynological material isolation process.

The sample solids are then transferred from the reaction cell to a centrifuge tube with dilute hydrochloric acid having a preferred concentration of about 0.5 to about 2.0 moles per liter. The sample is centrifuged in the dilute hydrochloric acid at about 2000 to about 3500 rpm for about 5 to about 20 minutes, most preferably about 10 minutes, in a benchtop centrifuge. All liquids are then removed from the centrifuge tube by aspirating or decanting the liquid. A wash of dilute (about 1M-8M) hydrochloric acid is usually needed at this point to prevent precipitation of zinc hydroxide.

A zinc bromide in deionized water solution is added to the tube. The solution should have a density of about 1.7 gm/ml. The zinc bromide solution and the sample solids are mixed well and centrifuged at about 500 to about 2000 rpm for about 10 to about 40 minutes, most preferably about 30 minutes, in a benchtop centrifuge. The sample solids and solution are then allowed to rest until layers formed within the tube are distinctly separated.

The top floating layer of organic light material comprising spores and pollen is transferred from the tube to a second centrifuge tube. Dilute hydrochloric acid is added to the second tube containing the spores and pollen, and the second tube is centrifuged at about 2000 to about 3500 rpm for about 5 to about 20 minutes, most preferably about 10 minutes.

The spores and pollen are washed at least one time with deionized water, followed by centrifugation to remove the water phase. Finally, the sample of palynological material comprising spores and pollen is suspended in sufficient deionized water for microscopical examination. Preferably the concentration for examination preparation will be about 5 to about 10 parts deionized water per part of spore and pollen residue.

In order to insure a more complete and accurate isolation, the first addition and removal steps of hydrochloric acid before the first flushing of reaction cell with deionized water are preferably repeated. It may also be desirable to sequentially repeat all steps after the second deionized water flushing step and before adding concentrated hydrofluoric acid for the second time. This repetition of steps should occur immediately before the second concentrated hydrofluoric acid addition step.

The mineral sample in the reaction cell is preferably agitated during reaction by injecting an inert gas into the reaction cell. Such agitation insures that the reaction will be more complete and will proceed at a faster rate. The inert gas used for agitation may be helium, argon, neon, and most preferably, nitrogen.

Total reaction time of the most preferred method is approximately 2 to 3 days. The inventors employ a reaction cell with an interior volume of about 125 ml. Within that cell a rock sample of about 10g to about 40g is processed. 50 ml of each reagent is preferably added for each step to the reaction cell. This amount is sufficient to completely cover the mineral sample.

This process is ideally suited for use with a computer-controlled apparatus for isolating bitumen kerogen, mineral and metal samples which is disclosed copending in U.S. Pat. Application Ser. No. 07/444,212, filed Dec. 1, 1989, commonly assigned.

The automated apparatus disclosed therein comprises one or more reaction cells, a measuring cell for providing a desired amount of fluid to the reaction cell, at least one sensor in the measuring cell for indicating a desired level of fluid, multiple fluid sources to be used for isolating the mineral samples, a fluid source valve for each fluid source to control the fluid flow from each fluid source to the measuring cell, a reaction cell valve for each reaction cell to control fluid flow between the measuring cell and the reaction cell, said reaction cell valve located between the measuring cell and the reaction cell, a waste dump valve to control fluid flow between the reaction cell and a waste dump, a back pressure regulator to provide for the safe release of excess pressure in the reaction cell and to moderate the reaction by releasing pressure, tubing to provide fluid communication between multiple fluid sources and the measuring cell, tubing to provide fluid communication between the measuring cell and the reaction cell valve, and between the reaction cell valve and the reaction cell, tubing to provide fluid communication between the reaction cell and a waste dump.

The above elements are controlled by a microprocessor control system which sequentially opens and closes the proper valves in the desired order to fill the measuring cell with the desired fluids, discharge the contents of the measuring cell into the reaction cell, and drain the fluid contents of the reaction cell into the waste dump or a fraction collector at the desired times. The reaction cell, measuring cell, valves and tubing are made of materials substantially inert to acidic and basic reagents.

The reaction cell is comprised of a central reaction chamber, a sample retaining means which divides the chamber into upper and lower chambers, a first port communicating with the lower chamber, a first filter means located between the first port and the lower chamber, a second port communicating with the upper chamber, and a second filter means located between the second port and the upper chamber.

The apparatus is ideal for the automated isolation of various compounds from a mineral matrix by the use of acidic and basic reagents to attack the mineral matrix and remove undesirable compounds or minerals, or remove desired compounds or minerals as a solute to be later collected. The apparatus is also useful for gas-solid reactions, gas-liquid reactions, and the acid digestion of rocks and metals. The primary utility of the apparatus is believed to be the initial extraction of bitumen and isolation of kerogen and spores and pollen from rock samples.

A related process for isolating kerogen and other minerals from rock samples which employs the same apparatus is disclosed in copending U.S. Pat. Application Ser. No. 07/459,486, filed, Jan. 2, 1990, commonly assigned.

The preferred procedure followed in our laboratory for the next phase of the invention method, centrifugal and zinc bromide separation of the pollen and spore material, is set forth in the following example. This example is presented for illustrative purposes only and should not be construed to limit the scope of the invention, which is defined in the claims that follow.

EXAMPLE

After the removal of undesirable minerals and compounds from the rock sample in the reaction cell, the sample is transferred into a clean 50 milliliter plastic centrifuge tube by washing with 10% concentrated hydrochloric acid in deionized water. The tube is shaken to mix the sample and acid. The tube is then filled with 10% concentrated hydrochloric acid and mixed by inversion. If only a small volume of hydrochloric acid is used for transfer, a separate dilute hydrochloric acid wash is employed.

The sample is centrifuged at about 2800 rpm for about 10 minutes in a benchtop centrifuge. The centrifuge we employ is an International Equipment Co. IEC Model Centra-8 centrifuge. This equipment can achieve a maximum of 2440 times gravity at the tip of the centrifuge tube.

All fluid is aspirated from the sample in the tube. Twenty milliliters of zinc bromide solution having a density of 1.7 gm/ml is added to the tube. The solution is prepared by dissolving 1000 grams of zinc bromide in 500 milliliters of deionized water, allowing the solution to cool, and then diluting with additional deionized water until a density of 1.7 is obtained with a hydrometer.

The sample is mixed with the zinc bromide solution with a wooden applicator stick and the tube is shaken. The tube is centrifuged for 30 minutes at about 1000 rpm and allowed to stand until the layers are distinctly separated within the tube. The separation is based upon the very slight differences in density between the spores and pollen and the suspending zinc bromide solution.

The floating spores and pollen are transferred to a second plastic centrifuge tube by decanting the floating materials into the second tube. Thirty milliliters of 6M hydrochloric acid is added to the floating material, followed by deionized water to fill the tube. The tube is shaken, centrifuged, and the liquid decanted carefully to retain the organic material in the bottom of the tube.

At this time, the pollen and spore material is stained with a water soluble red (in basic solution) stain to enable it to be easily discerned on finished slides under the microscope. Our procedure for staining begins by adding a few drops of 1% ammonium hydroxide to the sample residue. The weak base enables the microfossils to take on a deeper shade of red stain. Approximately 0.5 milliliters of 0.4% Safranin-O stain is added to each sample residue. The residue is vortexed to mix the contents for about 10 seconds to ensure thorough mixing. The amount of stain added is proportional to the volume of sample residue. We prefer to add about 0.5 milliliters of stain for each 5 millimeter depth of residue in the tube. The sample and stain are allowed to react for about 10 minutes. Deionized water is added to fill the tube at the end of reaction time in order to dilute the stain. The tube is centrifuged at about 2800 rpm for 15 seconds and decanted.

The stained residue is washed at least one time with deionized water, centrifuged at 2800 rpm and decanted. The tube is then filled with enough deionized water to suspend the residue in about 8 parts of deionized water per 1 part of residue.

The tube is shaken and a pollen and spore microscopical sample is prepared by placing a drop of the organic suspension on a clean coverslip. The sample is spread evenly on the coverslip, dried at about 30° C. on a slide warmer and mounted on a slide.

Many other variations and modifications may be made in the concepts described by those skilled in the art without departing from the concepts of the present invention. Accordingly, it should be clearly understood that the concepts disclosed in the description are illustrative only and are not intended as limitations on the scope of the invention.

What is claimed is:

1. A method for the isolation of palynological materials from a rock matrix sample in a pressurized reaction cell which comprises:

placing the rock sample in a reaction cell, said reaction cell permitting reaction at pressures greater than about two atmospheres and providing for removal of all liquids from the cell without significant loss of sample solids;

adding a mixture of concentrated hydrochloric acid and deionized water to the reaction cell;

removing the mixture from the reaction cell adding concentrated hydrochloric acid to the reaction cell;

removing the hydrochloric acid from the reaction cell flushing the reaction cell with deionized water to bring the rock sample relatively close to neutrality;

adding concentrated ammonium hydroxide to the reaction cell;

removing the ammonium hydroxide from the reaction cell flushing the reaction cell with deionized water to and bring the rock sample relatively close to neutrality;

adding concentrated hydrofluoric acid to the reaction cell;
removing the hydrofluoric acid from the reaction cell;
adding concentrated hydrochloric acid to the reaction cell;
removing the hydrochloric acid from the reaction cell;
flushing the reaction cell with deionized water;
adding concentrated ammonium hydroxide to the reaction cell;
removing the ammonium hydroxide from the reaction cell;
adding concentrated hydrofluoric acid to the reaction cell;
removing the hydrofluoric acid from the reaction cell;
flushing the reaction cell with deionized water;
adding concentrated ammonium hydroxide to the reaction cell;
removing the ammonium hydroxide from the reaction cell;
flushing the reaction cell with deionized water;
adding concentrated hydrochloric acid to the reaction cell;
removing the hydrochloric acid from the reaction cell;
flushing the reaction cell with deionized water;
adding concentrated ammonium hydroxide to the reaction cell;
removing the ammonium hydroxide from the reaction cell;
flushing the reaction cell with deionized water;
adding concentrated nitric acid to the reaction cell;
removing the nitric acid from the reaction cell;
flushing the reaction cell with deionized water;
transferring a sample comprising solids in dilute hydrochloric acid from the reaction cell to a centrifuge tube;
centrifuging the sample at about 2000 to about 3500 rpm for about 5 to about 20 minutes in a benchtop centrifuge;
removing all liquid from the centrifuge tube;
washing the sample with dilute hydrochloric acid;
adding a zinc bromide in deionized water solution to the tube, said solution having a density of about 1.7 gm/ml;
mixing the zinc bromide solution and the sample in the tube;
centrifuging the tube at about 500 to about 2000 rpm for about 10 to about 40 minutes in said benchtop centrifuge;
allowing the sample and solution to rest until layers form within the tube;
transferring a top floating layer of organic light material comprising spores and pollen from the tube to a second centrifuge tube;
adding dilute hydrochloric acid to the second tube;
centrifuging the second tube at about 2000 to about 3500 rpm for about 5 to about 20 minutes in said benchtop centrifuge;
washing the spores and pollen at least one time with deionized water;
centrifuging the second tube with spores and pollen to remove the water phase; and
suspending the spores and pollen in sufficient deionized water for microscopical examination.

2. The method of claim 1, futher comprising adding dilute hydrochloric acid to the reaction cell and later removing the hydrochloric acid from the reaction cell before transferring the sample to a said first centrifuge tube and after the last flushing of the reaction cell with deionized water.

3. The method of claim 1, wherein the dilute hydrochloric acid has a concentration of about 1.0 to about 8.0 moles per liter.

4. The method of claim 1, wherein the concentrated nitric acid has a concentration of about 10 to about 20 moles per liter.

5. The method of claim 1, wherein the spores and pollen are suspended in about 5 to about 10 parts of deionized water per part of spore and pollen residue for microscopical examination.

6. The method of claim 1, further comprising staining the spore and pollen sample to make microscopical examination easier.

7. The method of claim 1, further comprising repeating the first addition and removal steps of hydrochloric acid before the first flushing of the reaction cell with deionized water.

8. The method of claim 1, wherein the acid/base treatment steps, prior to the first centrifugation step, are performed at an elevated temperature of about 45° to about 65° C. and an elevated pressure of about 2 to about 5 atmospheres.

9. The method of claim 8, wherein said first mixture of hydrochloric acid and deionized water is reacted with the rock sample in the reaction cell for a time greater than about 15 minutes.

10. The method of claim 8, wherein the concentrated hydrochloric acid is reacted with the rock sample for a time greater than about 45 minutes.

11. The method of claim 8, wherein all the deionized water flushing steps occur for a time greater than about 15 minutes.

12. The method of claim 8, wherein the concentrated ammonium hydroxide is reacted with the rock sample for a time greater than about 15 minutes.

13. The method of claim 8, wherein the concentrated hydrofluoric acid is reacted with the rock sample for a time greater than about 45 minutes.

14. The method of claim 8, wherein the concentrated nitric acid is reacted with the rock sample for a time greater than about 10 minutes.

15. The method of claim 1, wherein the concentrated hydrochloric acid has a concentration of about 10 to about 12 molar.

16. The method of claim 1, wherein the concentrated hydrofluoric acid has a concentration of about 13 to about 35 molar.

17. The method of claim 1, wherein the concentrated ammonium hydroxide has a concentration of about 10 to about 20 molar.

18. The method of claim 1, wherein reagents and dissolved materials are removed from the reaction cell by drainage through a filter at the bottom of the reaction cell.

19. The method of claim 1, further comprising agitating the rock sample in the reaction cell during reaction with added reagents by injecting an inert gas into the reaction cell.

20. The method of claim 19, wherein the inert gas is selected from the ground consisting of nitrogen, helium, argon, and neon.

21. A method for the isolation of palynological material from a rock matrix sample in a pressurized reaction cell which comprises:

placing the rock sample in a reaction cell;

said reaction cell permitting reaction at pressures greater than about 2 atmospheres and temperatures between about 45° C. and about 65° C. and providing for removal of all liquids from the cell without significant loss of sample solids;

adding a mixture of concentrated hydrochloric acid and deionized water to the reaction cell and permitting reaction for a time greater than about 15 minutes at about 45° C. to about 65° C.;

removing the mixture from the reaction cell adding concentrated hydrochloric acid to the reaction cell and permitting reaction for a time greater than about 45 minutes at about 45° C. to about 65° C.;

removing the hydrochloric acid from the reaction cell;

flushing the reaction cell with deionized water to bring the rock sample relatively close to neutrality;

adding concentrated ammonium hydroxide to the reaction cell and permitting reaction for a time greater than about 15 minutes at about 45° C. to about 65° C.;

removing the ammonium hydroxide from the reaction cell;

flushing the reaction cell with deionized water to bring the rock sample relatively close to neutrality;

adding concentrated hydrofluoric acid to the reaction cell and permitting reaction for a time greater than about 45 minutes at about 45° C. to about 65° C.;

removing the hydrofluoric acid from the reaction cell;

adding concentrated hydrochloric acid to the reaction cell and permitting reaction for a time greater than about 45 minutes at about 45° C. to about 65° C.;

removing the hydrochloric acid from the reaction cell;

flushing the reaction cell with deionized water to and bring the rock sample relatively close to neutrality;

adding concentrated ammonium hydroxide to the reaction cell and permitting reaction for a time greater than about 15 minutes at about 45° C. to about 65° C.;

removing the ammonium hydroxide from the reaction cell;

adding concentrated hydrofluoric acid to the reaction cell and permitting reaction for a time greater than about 45 minutes at about 45° C. to about 65° C.;

removing the hydrofluoric acid from the reaction cell;

flushing the reaction cell with deionized water to bring the rock sample relatively close to neutrality;

adding concentrated ammonium hydroxide to the reaction cell and permitting reaction for a time greater than about 15 minutes at about 45° C. to about 65° C.;

removing the ammonium hydroxide from the reaction cell;

flushing the reaction cell with deionized water to and bring the rock sample relatively close to neutrality;

adding concentrated hydrochloric acid to the reaction cell and permitting reaction for a time greater than about 45 minutes at about 45° C. to about 65° C.;

removing the hydrochloric acid from the reaction cell;

flushing the reaction cell with deionized water to bring the rock sample relatively close to neutrality;

adding concentrated ammonium hydroxide to the reaction cell and permitting reaction for a time greater than about 15 minutes at about 45° C. to about 65° C.;

removing the ammonium hydroxide from the reaction cell;

flushing the reaction cell with deionized water to bring the rock sample relatively close to neutrality;

adding concentrated nitric acid to the reaction cell and permitting reaction for a time greater than about ten minutes at about 45° C. to about 65° C.;

removing the nitric acid from the reaction cell;

flushing the reaction cell with deionized water to bring the rock sample relatively close to neutrality;

transferring a sample comprising solids in dilute hydrochloric acid from the reaction cell to a centrifuge tube;

centrifuging the sample at about 2000 to about 3500 rpm for about 5 to about 20 minutes in a benchtop centrifuge;

removing all liquids from the centrifuge tube;

washing the sample with dilute hydrochloric acid;

adding a zinc bromide in deionized water solution to the tube, said solution having a density of about 1.7 gm/ml;

mixing the zinc bromide solution and the sample in the tube;

centrifuging the tube at about 500 to about 2000 rpm for about 10 to about 40 minutes in said benchtop centrifuge;

allowing the sample and solution to rest until layers formed within the tube are separated;

transferring a top floating layer of organic light material comprising spores and pollen from the tube to a second centrifuge tube;

adding dilute hydrochloric acid to the second tube;

centrifuging the second tube at about 2000 to about 3500 rpm for about 5 to about 20 minutes in said benchtop centrifuge;

washing the spores and pollen at least one time with deionized water;

centrifuging the second tube with spores and pollen to remove the water phase; and suspending the sample of spores and pollen in sufficient deionized water for microscopical examination.

* * * * *

UNITED STATES PATENT AND TRADEMARK OFFICE
CERTIFICATE OF CORRECTION

PATENT NO. : 5,098,844
DATED : March 24, 1992
INVENTOR(S) : David Gerald Nolte and Rae Anderson Royle It is certified that error appears in the above-indentified patent and that said Letters Patent is hereby corrected as shown below:

Column 10, line 4, please delete "a".

In Column 10, line 67, please substitute --group-- for "ground".

In Column 11, line 44, please delete "and".

Signed and Sealed this

Fourth Day of October, 1994

Attest:

BRUCE LEHMAN

Attesting Officer     Commissioner of Patents and Trademarks